US012559482B2

(12) United States Patent (10) Patent No.: US 12,559,482 B2
Cheng et al. (45) Date of Patent: Feb. 24, 2026

(54) METHOD FOR EXTRACTING MUPIROCIN

(71) Applicant: HANGZHOU ZHONGMEIHUADONG PHARMACEUTICAL CO., LTD, Hangzhou (CN)

(72) Inventors: Zhaobing Cheng, Hangzhou (CN); Guanghui Kou, Hangzhou (CN); Yiming Xu, Hangzhou (CN); Kai Zhang, Hangzhou (CN); Yuchen Zhang, Hangzhou (CN)

(73) Assignee: HANGZHOU ZHONGMEIHUADONG PHARMACEUTICAL CO., LTD, Zhejiang (CN)

( * ) Notice: Subject to any disclaimer, the term of this patent is extended or adjusted under 35 U.S.C. 154(b) by 464 days.

(21) Appl. No.: 18/022,806

(22) PCT Filed: Aug. 11, 2021

(86) PCT No.: PCT/CN2021/111926
§ 371 (c)(1),
(2) Date: Feb. 23, 2023

(87) PCT Pub. No.: WO2022/042299
PCT Pub. Date: Mar. 3, 2022

(65) Prior Publication Data
US 2023/0312540 A1 Oct. 5, 2023

(30) Foreign Application Priority Data

Aug. 25, 2020 (CN) .......................... 202010864243.5
Nov. 12, 2020 (CN) .......................... 202011258583.X

(51) Int. Cl.
*C07D 407/06* (2006.01)
*B01D 11/04* (2006.01)
*B01D 15/08* (2006.01)

(52) U.S. Cl.
CPC ........ *C07D 407/06* (2013.01); *B01D 11/0492* (2013.01); *B01D 15/08* (2013.01)

(58) Field of Classification Search
CPC ...................................................... C07D 407/06
USPC ........................................................ 514/460
See application file for complete search history.

(56) References Cited

U.S. PATENT DOCUMENTS 4,222,942 A 9/1980 O'Hanlon et al.
7,619,102 B2 11/2009 Bisschops et al.

FOREIGN PATENT DOCUMENTS

| CN | 1345377 A | 4/2002 |
| CN | 101591333 A | 12/2009 |
| CN | 102863433 A | 1/2013 |
| CN | 109053707 A | 12/2018 |
| CN | 110606844 A | 12/2019 |
| JP | 52-70083 A | 6/1977 |

OTHER PUBLICATIONS

International Search Report mailed Nov. 11, 2021 in PCT application PCT/CN2021/111926, 6 pages.
Written Opinion mailed Nov. 11, 2021 in PCT application PCT/CN2021/111926, 4 pages.

*Primary Examiner* — Taofiq A Solola
(74) *Attorney, Agent, or Firm* — NIXON & VANDERHYE, PC

(57) ABSTRACT

A method for extracting mupirocin. The main steps thereof comprise: resin adsorption, desorption and concentration, multi-step extraction, and dehydration and decoloration, wherein the multi-step extraction comprises at least one ester solvent extraction and at least one alkaline water extraction. The method is suitable for industrialization, the extraction recovery rate of mupirocin is 80% or more, and the purity of the mupirocin is 80% or more.

6 Claims, No Drawings

METHOD FOR EXTRACTING MUPIROCIN

REFERENCE TO RELATED APPLICATIONS

This application is the U.S. national phase of International Application No. PCT/CN2021/111926 filed Aug. 11, 2021 which designated the U.S. and claims priority to CN 202011258583.X filed Nov. 12, 2020, and CN 202010864243.5 filed Aug. 25, 2020, the entire contents of each of which are hereby incorporated by reference.

TECHNICAL FIELD

The present invention relates to the technical field of pharmaceuticals, particularly to the technical field of fermentation, and more particularly to a method for extracting mupirocin fermentation broth.

BACKGROUND

Mupirocin (pseudomonic acid A), is an aminoacyl transaminase inhibitor antibiotic that specifically binds to the isoleucyl-tRNA synthetase in bacteria, thereby inhibiting the synthesis of isoleucine-containing proteins in bacteria. It can effectively resist various gram-positive bacteria including *Staphylococcus aureus, Streptococcus amimiferus, Staphylococcus epidermidis, Streptococcus pneumoniae, Streptococcus pyogenes*, etc., and some gram-negative bacteria including *Haemophilus influenzae*, etc. Mupirocin has no cross-drug resistance with other antibiotics, demonstrating higher medical value. It has long been clinically applied, and is sold under the trade name Bactroban® or mupirocin ointment.

Patent No. CN109053707A relates to a method for purifying mupirocin, which extracts mupirocin by filtering or concentrating a fermentation broth through a filter membrane. The temperature of the filter membrane usually rises during use of the filter membrane and will affect the purity of mupirocin due to the existence of thermosensitive impurities. Therefore, the method requires strict condition control and thus is not suitable for industrial production. U.S. Pat. No. 7,619,102 relates to a method where mupirocin is precipitated from an aqueous solution thereof and recovered. The method has a lower yield and a higher requirement for removing moisture after precipitation. U.S. Pat. No. 4,222,942 relates to a method similar to the present invention, which extracts a mupirocin extract using a polar water-insoluble organic solvent. However, the method has a lower yield and is not suitable for release production due to the incompatibility between the solvent and the diluent.

That is, the methods described above have unsatisfactory aspects in terms of strict process control conditions, environmental requirements and commercial or ecological perspectives. Therefore, there is still a need for new methods for purifying mupirocin that are suitable for industrial mass production and are environment-friendly and cost controllable.

On this basis, the present invention provides an extraction method of high extraction rate and safety, suitability for industrialization and cost-efficiency. Based on the structure and fermentation process of mupirocin, the method combines and optimizes the procedures such as resin absorption, desorption and concentration, extraction, and dehydration and decoloration, and thus completes the efficient purification of mupirocin. The present invention provides certain technical support for improving the mupirocin production technology of enterprises and the productivity of the industry.

SUMMARY

The present invention provides a method for extracting mupirocin suitable for industrial mass production. In particular, the method comprises adsorbing mupirocin with a resin, desorbing to obtain a desorption solution, concentrating the desorption solution, and further extracting, dehydrating and decolorizing.

To overcome the defects in the prior art, the present application realizes maximal transfer of the active ingredient in the organic phase by adjusting the pH to convert mupirocin into an ester-soluble free carboxylic acid and a water-soluble base, and further removes impurities with distinct greatly properties from mupirocin in the above two extraction steps. Through the above procedures, the method disclosed herein well controls the content of impurities, improves the purification process and ensures the quality of the finished product, while ensuring the yield.

Mupirocin involved in the present invention may be synthesized by fermentation or may naturally exist. The mupirocin solution involved in the present invention is obtained by conventional fermentation technology and may be a mupirocin fermentation broth, an aqueous mupirocin solution, a filtrate containing mupirocin obtained by filtration, or a supernatant containing mupirocin obtained by centrifugation.

The present invention uses a macroporous resin with a pore size matching the molecular weight of mupirocin to ensure the efficiency of the adsorption, and the resin can be used on a large scale and can be recycled, which is beneficial to mass production of the whole extraction process and cost-efficient.

Acetone or ethyl acetate is used for desorption in the present invention, and the selection of the desorption solvent brings surprising technical effects to the method of the present invention. When acetone is used for desorption, it is not only performs desorption, but also facilitates the activation and regeneration of the macroporous resin in the desorption column. When ethyl acetate is used for desorption, it is not only desorption solvent, but also preferred in the extraction steps, thus limiting the introduction of other reagents in the extraction steps and minimizing the possibility of introducing impurities due to the consistency of the reagent in multiple steps.

The yield of the method for extracting mupirocin disclosed herein can reach 90% and the purity of the mupirocin may be 80% or higher.

Using the above forms of mupirocin, the present invention is intended to provide a method for extracting mupirocin comprising an extraction procedure that is a multi-step extraction comprising at least one ester solvent extraction and at least one alkaline water extraction.

Specifically, the present invention provides a method for extracting mupirocin, comprising:
- a. resin adsorption: adding the resin into a mupirocin fermentation broth and stirring for adsorption, filtering the fermentation broth, rinsing, and collecting the resin;
- b. desorption and concentration: loading the resin collected in step a on a desorption column; soaking the resin with ethyl acetate or acetone, desorbing, and collecting and concentrating the desorption solution;
- c. extraction: extracting the concentrated desorption solution collected in step b, converting mupirocin into an ester-soluble free carboxylic acid and/or a water-soluble base by adjusting the pH value, and separating a solvent phase;

d. dehydration and decoloration: dehydrating and/or decoloring the solvent phase collected in step c in sequence.

As a specific embodiment, in step c, the concentrated desorption solution collected in step b is extracted using an ester solvent and/or alkaline water; more preferably, the extraction is conducted in steps with solvents being independently selected as required.

As a specific embodiment, in step d, the amount of the dehydrating agent used is 0.02 to 0.08 kg/L solvent phase; the amount of the decolorant used is 1 to 6 g/g dehydrated solvent phase.

Mupirocin involved in the present invention may be synthesized by fermentation or may naturally exist.

The mupirocin solution involved in the present invention is obtained by conventional fermentation technology or may be a mupirocin fermentation broth, an aqueous mupirocin solution, a filtrate containing mupirocin obtained by filtration, or a supernatant containing mupirocin obtained by centrifugation.

Mupirocin is directly extracted and obtained and can be converted into mupirocin calcium if needed in the present invention. Different from the method of preparing mupirocin calcium which is difficult to convert into mupirocin, the present invention ensures the flexibility of the final product and can better adapt to the requirements of the terminal market.

As a specific embodiment, the resin in step a is a nonpolar macroporous adsorption resin and is selected from AB-8 resin, H103 resin, X-5 resin, H107 resin or D3520 resin, preferably H103 resin.

As a specific embodiment, the pore size of the resin in step a matches the molecular weight of mupirocin, thus ensuring the extent of adsorption.

As a specific embodiment, the feeding amount of the resin in step a is 0.01 to 0.05 g/g fermentation broth, preferably 0.02 to 0.04 g/g fermentation broth.

As a specific embodiment, the pH of the resin adsorption in steps a and b is 5.0 to 7.0, preferably 5.5 to 6.5.

As a specific embodiment, the amount of acetone used for the desorption in step b is 2 to 5 times the volume of the resin, wherein acetone serves as the desorption solvent while facilitating the activation and regeneration of the resin in the desorption column.

As a specific embodiment, the amount of ethyl acetate used for the desorption in step b is 2 to 5 times the volume of the resin, wherein ethyl acetate is used for desorption and is also preferred in the extraction steps, thus limiting the introduction of other reagents in the extraction steps and minimizing the possibility of introducing impurities due to the consistency of the reagent in multiple steps.

As a specific embodiment, after collecting and concentrating the desorption solution in step b, the aqueous phase should be retained for step c; the retained aqueous phase refers to the residual aqueous phase in the process of the resin adsorption and/or water contained in acetone.

As a specific embodiment, the flow rate of desorption in step b is 1/5 to 6/5 times the volume of the resin per hour, preferably 3/5 to 6/5 times the volume of the resin per hour.

As a specific embodiment, the extraction in step c is a multi-step extraction comprising at least one ester solvent extraction and at least one alkaline water extraction.

As a specific embodiment, the extraction in step c comprises a first ester solvent extraction, an alkaline water extraction and a second ester solvent extraction.

As a specific embodiment, in the alkaline water extraction in step c, the alkaline water is selected from a sodium bicarbonate solution, an ammonium bicarbonate solution and a sodium hydroxide solution.

As a specific embodiment, in the alkaline water extraction in step c, the alkaline water has a pH of 7.0 to 10.0, preferably 7.5 to 9.0.

As a specific embodiment, the ester solvent in the extraction is selected from diisooctyl phosphate, tributyl phosphate, ethyl acetate, isopropyl acetate or butyl acetate, preferably ethyl acetate.

As a specific embodiment, the ester solvent in the extraction has a pH of 3.0 to 5.0, preferably 3.0 to 4.5.

As a specific embodiment, the first ester solvent extraction may be repeated once or twice, and the ester solvent phases separated from the extractions are combined.

As a specific embodiment, the alkaline water extraction may be performed once or twice or more, and the alkaline water phases separated from the extractions are combined for later use in the second ester solvent extraction.

As a specific embodiment, the second ester solvent extraction may be repeated once or twice, and the ester solvent phases separated from the extractions are combined.

In the multi-step extraction according to the present invention, the number of the alkaline water extractions is directly related to the initial titer of mupirocin fermentation broth. For fermentation broth with a titer greater than 3000 μg/mL, the alkaline water extraction is usually performed at least twice and for fermentation broth with a titer greater than 6000 μg/mL, the alkaline water extraction is usually performed at least thrice.

As a specific embodiment, the dehydrating agent in step d is selected from anhydrous sodium sulfate, anhydrous magnesium sulfate or anhydrous calcium sulfate, preferably anhydrous sodium sulfate.

As a specific embodiment, the decolorant in step d is selected from activated carbon or activated clay, preferably 8815 activated carbon.

The present invention optimizes the process conditions in each step. For example, the pH of the resin adsorption is 4.0 to 7.0, preferably 5.5 to 6.5, where mupirocin can be better extracted from the concentrated desorption solution with the ester solvent; the ester solvent in the extraction has a pH of 3.0 to 5.0, preferably 3.0 to 4.5, where mupirocin can be better extracted from the ester extract with the alkaline water, such that the steps of the whole extraction process match with each other to form an integrated whole.

Repeated studies and experiments demonstrated that the method for extracting mupirocin disclosed herein can reach a yield of 80% or higher. As a specific embodiment, the method for extracting mupirocin disclosed herein can reach a yield of 85% or 90%, or even 95%.

The present invention has the following beneficial effects:

1. The present invention uses organic solvent extraction instead of the conventional precipitation recovery method. The extraction disclosed herein is a multi-step extraction comprising at least one ester solvent extraction and at least one alkaline water extraction. By designing the conditions and times of the ester solvent extraction and the alkaline water extraction, and designing a plurality of sub-extractions and the reasonable combination of fractions in each extraction, the method full transfers the fermentation titer of mupirocin, and is thus particularly suitable for the extraction of mupirocin fermentation broth with a titer greater than 5000 μg/mL, thereby ensuring the yield in mass process production.

2. The present invention selects ethyl acetate or acetone for desorption. The selection of ethyl acetate matches the organic solvent in the extraction steps, minimizing the possibility of introducing impurities. The selection of acetone facilitates the activation and regeneration of the macroporous resin. The alternative selection of the two desorption reagents reduces the risk of introducing impurities or reduces the process cost, thus achieving the goal of killing two birds with one stone.

3. In industrial production, the extraction method disclosed herein can treat mupirocin fermentation broth on a kilogram scale and maintain a stable yield of 80%, up to 95%. In addition, the purity of mupirocin is always kept over 80% in the extraction process, thereby laying a good foundation for the subsequent refining processes. The method disclosed herein is fully suitable for the scale of industrial production and maximizes the yield and the product purity unter the condition that the quality meets the national approval standards.

DETAILED DESCRIPTION

The present invention will be further illustrated in detail with reference to the following specific examples. The following examples is only intended to help understand the method of the present invention and its core concepts. Any possible changes and substitutions can be made by those skilled in the art without departing from the spirit of the present invention, and these changes and substitutions are all within the scope of the present invention. Experimental procedures without specific conditions indicated in the following examples of the present invention are generally conducted according to conventional conditions, or according to conditions recommended by the manufacturers of the starting materials or commercial products. Reagents without specific sources indicated are generally commercially available conventional reagents.

EXAMPLE 1. EXTRACTION OF MUPIROCIN a. Resin Adsorption:

A mupirocin fermentation broth was added into a pretreatment tank and the volume was measured. The broth was stirred, and the pH was adjusted to 6.0 with 2 N hydrochloric acid or 2 N sodium hydroxide.

Half an hour after pretreatment, H103 resin was added into the pretreatment tank at a feed amount of 0.04 g mupirocin/g resin. The mixture was stirred for 4.5 h at room temperature for adsorption. After the completion of the adsorption, the stir was stopped. The fermentation broth was filtered through a 40-mesh vibrating screen, and the surface of the resin was rinsed with drinking water to remove the adhered bacteria residues. The resin was collected (95.5% yield).

b. Desorption and Concentration:

The resin was evenly loaded into a desorption column and washed reversely with drinking water more than 2 times the volume of the resin until the color of the water became light. The column was purged with air to remove the drinking water, and acetone was introduced reversely until the resin was completely soaked in acetone. The timing was started when the resin was completely soaked in acetone. After 2 hours, the desorption was performed at a flow rate of 3/5 times the volume of the resin per hour. The amount of acetone used for desorption was about 3 times the volume of the resin. The desorption solution was collected and the resin was washed with drinking water until the system was free of acetone smell. The mupirocin content in the desorption solution was 78.5%. The desorption solution was pumped into an acetone concentration tank and concentrated at an internal temperature below 50.0° C. until acetone was absent. The aqueous phase was retained.

c. Extraction:

The first ester solvent extraction: The aqueous phase was pumped into an extraction tank. The pH was adjusted to 4.5 with 2 N hydrochloric acid. Ethyl acetate of ½ the aqueous phase volume was added. The mixture was stirred for 45 minutes at room temperature, and left to stand for 30 minutes. The ethyl acetate phase was separated. The above procedures were repeated once. The ethyl acetate phases separated from the two extractions were combined.

The first alkaline water extraction: The combined ethyl acetate phases were pumped into an extraction tank. A 2.5% ammonium bicarbonate solution of ⅓ the ethyl acetate phase volume was added. The mixture was stirred for 30 minutes at room temperature, and left to stand for 30 minutes. The alkaline water phase was separated. The above procedures were repeated thrice. The alkaline water phases separated from the four extractions were combined. The solvent of the ethyl acetate phase was recovered.

The second ester solvent extraction: The combined alkaline water phases were pumped into an extraction tank. The pH was adjusted to 4.0 by dropwise adding 2 N hydrochloric acid. Ethyl acetate of ½ the aqueous phase volume was added. The mixture was stirred for 45 minutes at room temperature, and left to stand for 30 minutes. The ethyl acetate phase was separated. The above procedures were repeated once. The ethyl acetate phases separated from the two extractions were combined. After extraction, the yield of mupirocin was 85.3%.

d. Dehydration and Decoloration:

Anhydrous sodium sulfate was added at 2.3 kg/50 L combined ethyl acetate phases, and the mixture was stirred for dehydration for 30 minutes. The ethyl acetate phase was separated. After dehydration, the dehydrated anhydrous sodium sulfate was washed with fresh ethyl acetate in an amount of 1.5 times the weight of the anhydrous sodium sulfate added. The dehydrated ethyl acetate phase was decolorized according to a ratio of 3 g/g 8815 activated carbon. The activated carbon was washed with fresh ethyl acetate in an amount of 2 times the weight of the activated carbon added after decolorization. Finally, mupirocin was obtained with a yield of 83.3% and a content of 80.2%.

EXAMPLE 2. EXTRACTION OF MUPIROCIN a. Resin Adsorption:

A fermentation broth was added into a pretreatment tank and the volume was measured. The broth was stirred, and the pH was adjusted to 6.0 with 2 N hydrochloric acid or 2 N sodium hydroxide.

Half an hour after pretreatment, H103 resin was added into the pretreatment tank at a feed amount of 0.03 g mupirocin/g resin. The mixture was stirred for 4 h at room temperature for adsorption. After the completion of the adsorption, the stir was stopped. The fermentation broth was filtered through a 40-mesh vibrating screen, and the surface of the resin was rinsed with drinking water to remove the adhered bacteria residues. The resin was collected (94.7% yield).

b. Desorption and Concentration:

The resin was evenly loaded into a desorption column and washed reversely with drinking water more than 2 times the volume of the resin until the color of the water became light. The column was purged with air to remove the drinking water, and acetone was introduced reversely until the resin was completely soaked in acetone. The timing was started when the resin was completely soaked in acetone. After 2 hours, the desorption was performed at a flow rate of 7/10 times the volume of the resin per hour. The amount of acetone used for desorption was about 3.5 times the volume of the resin. The desorption solution was collected and the resin was washed with drinking water until the system was free of acetone smell. The desorption solution was pumped into an acetone concentration tank and concentrated at a vacuum pressure below −0.08 MPa, a hot water tank temperature at 70.0° C. and an internal temperature below 50.0° C. until acetone was absent. The aqueous phase was retained.

c. Extraction:

The first ester solvent extraction: The aqueous phase was pumped into an extraction tank. The pH was adjusted to 3.5 with 2 N hydrochloric acid. Ethyl acetate of ½ the aqueous phase volume was added. The mixture was stirred for 45 minutes at room temperature, and left to stand for 30 minutes. The ethyl acetate phase was separated. The above procedures were repeated once. The ethyl acetate phases separated from the two extractions were combined.

The first alkaline water extraction: The combined ethyl acetate phases were pumped into an extraction tank. A 2% ammonium bicarbonate solution of ⅓ the ethyl acetate phase volume was added. The mixture was stirred for 30 minutes at room temperature, and left to stand for 30 minutes. The alkaline water phase was separated. The above procedures were repeated thrice. The alkaline water phases separated from the four extractions were combined. The solvent of the ethyl acetate phase was recovered.

The second ester solvent extraction: The combined alkaline water phases were pumped into an extraction tank. The pH was adjusted to 4.0 by dropwise adding 2 N hydrochloric acid. Ethyl acetate of ½ the aqueous phase volume was added. The mixture was stirred for 45 minutes at room temperature, and left to stand for 30 minutes. The ethyl acetate phase was separated. The above procedures were repeated once. The ethyl acetate phases separated from the two extractions were combined. After the extraction, the yield of mupirocin was 87.3%, and the content of mupirocin was 82.5%.

EXAMPLE 3. INVESTIGATION ON RESIN ADSORPTION OF MUPIROCIN

Resin adsorption: A fermentation broth was added into a pretreatment tank and the volume was measured. The broth was stirred, and the pH was adjusted to 6.0 with hydrochloric acid or sodium hydroxide. Half an hour after pretreatment, H103 resin was added into the pretreatment tank at a feed amount of 0.02 g mupirocin/g resin. The mixture was stirred for 4 h at room temperature for adsorption. After the completion of the adsorption, the stir was stopped. The fermentation broth was filtered through a 40-mesh vibrating screen, and the surface of the resin was rinsed with drinking water to remove the adhered bacteria residues. The resin was collected (94.5% yield).

The other procedures were the same as those in Example 2, with an overall mupirocin yield of 82.3% and a purity of 82.0%.

EXAMPLE 4. INVESTIGATION ON DESORPTION AND CONCENTRATION OF MUPIROCIN

In the desorption step of the process for extracting mupirocin, mupirocin in the desorption column is eluted from the resin into acetone or ethyl acetate. To make the adsorption method applicable to industrial mass production, in addition to the adsorption and desorption described above, other conditions such as space velocity (volume flow rate/resin volume), the geometry of resin column bed (height/diameter ratio), the structure of the column bed, operation procedures and the like are also required to cooperate, wherein space velocity tends to be a main influencing factor.

Desorption and concentration: The resin was evenly loaded into a desorption column and washed reversely with drinking water more than 2 times the volume of the resin until the color of the water became light. The column was purged with air to remove the drinking water, and ethyl acetate was introduced reversely until the resin was completely soaked in ethyl acetate. The timing was started when the resin was completely soaked in ethyl acetate. After 2 hours, the desorption was performed at a flow rate of 7/10 times the volume of the resin per hour for 5 h. The amount of ethyl acetate used for desorption was about 4 times the volume of the resin. The desorption solution was collected and the resin was washed with drinking water. The mupirocin content in the desorption solution was 86.9%. The other procedures were the same as those in Example 1, with an overall mupirocin yield of 86.0% and a purity of 80.5%.

EXAMPLE 5. INVESTIGATION ON DESORPTION AND CONCENTRATION OF MUPIROCIN

Desorption and concentration: The resin was evenly loaded into a desorption column and washed reversely with drinking water more than 2 times the volume of the resin until the color of the water became light. The column was purged with air to remove the drinking water, and acetone was introduced reversely until the resin was completely soaked in acetone. The timing was started when the resin was completely soaked in acetone. After 2 hours, the desorption was performed at a flow rate of 1/5 times the volume of the resin per hour for 10 h. The amount of acetone used for desorption was about 4 times the volume of the resin. The desorption solution was collected and the resin was washed with drinking water until the system was free of acetone smell. The mupirocin content in the desorption solution was 88.5%.

EXAMPLE 6. INVESTIGATION ON EXTRACTION OF MUPIROCIN

The first ester solvent extraction: The aqueous phase was pumped into an extraction tank. The pH was adjusted to 5.0 with hydrochloric acid. Ethyl acetate of ½ the aqueous phase volume was added. The mixture was stirred for 45 minutes at room temperature, and left to stand for 30 minutes. The ethyl acetate phase was separated. The above procedures were repeated once. The ethyl acetate phases separated from the two extractions were combined.

The first alkaline water extraction: The combined ethyl acetate phases were pumped into an extraction tank. A 2% ammonium bicarbonate solution of ⅓ the ethyl acetate phase volume was added. The mixture was stirred for 30 minutes at room temperature, and left to stand for 30 minutes. The alkaline water phase was separated. The above procedures were repeated four times. The alkaline water phases separated from the four extractions were combined. The solvent of the ethyl acetate phase was recovered.

The second ester solvent extraction: The combined alkaline water phases were pumped into an extraction tank. The pH was adjusted to 4.0 by dropwise adding hydrochloric acid. Ethyl acetate of ½ the aqueous phase volume was added. The mixture was stirred for 45 minutes at room temperature, and left to stand for 30 minutes. The ethyl acetate phase was separated. The above procedures were repeated once. The ethyl acetate phases separated from the two extractions were combined. After extraction, the relative yield of mupirocin was 95.5%.

The other procedures were the same as those in Example 1, with an overall mupirocin yield of 82.0% and a purity of 82.5%.

EXAMPLE 7. NECESSITY OF MULTI-STEP EXTRACTION IN MUPIROCIN EXTRACTION

1. Only one ester solvent extraction in the extraction step: The aqueous phase after desorption and concentration was pumped into an extraction tank. The pH was adjusted to 3.5 with hydrochloric acid. A proper amount of ethyl acetate was added. The mixture was stirred and left to stand. The ethyl acetate phase was separated. The above procedures were repeated once, and the ethyl acetate phases separated from the two extractions were combined. After one ester solvent extraction, the yield of mupirocin was 80.5%, and the purity was 78.1%.

Only one alkaline water extraction in the extraction step: The aqueous phase after desorption and concentration was pumped into an extraction tank. The alkaline water and the aqueous phase are of the same polarity and thus cannot be separated, and the extraction cannot be performed.

More than one ester solvent extraction in the extraction step: The aqueous phase after desorption and concentration was pumped into an extraction tank. The pH was adjusted to 3.5 with hydrochloric acid. A proper amount of ethyl acetate was added. The mixture was stirred and left to stand. The ethyl acetate phase was separated. The above procedures were repeated twice, and the ethyl acetate phases separated from the three extractions were combined. After two ester solvent extractions, the yield of mupirocin was 82.0%, and the purity was 78.5%.

EXAMPLE 8. INVESTIGATION ON AMOUNT OF RESIN USED IN RESIN ADSORPTION OF MUPIROCIN

A mupirocin fermentation broth was taken and the mupirocin content was calculated in the fermentation broth. The resin was added at an amount of 0.02, 0.03 or 0.04 g mupirocin/g resin. The mixture was stirred for adsorption for 4, 6, 8 or 24 hours and then filtered. The content of mupirocin in the filtrate was detected. The fermentation titers after adsorption were 278, 217, 137, 85, 385, 293, 238, 194, 446, 386, 340 and 322, respectively.

EXAMPLE 9. REPRODUCTION OF METHOD FOR EXTRACTING PSEUDOMONIC ACID A DESCRIBED IN CN101591333B (Example 1, i.e., the method described in paragraphs [0041] to [0044], which reports that the content of pseudomonic acid A in the desorption solution reaches 70% and the yield of pseudomonic acid A reaches 90%)

25 L of mupirocin fermentation broth (the concentration of pseudomonic acid A was 6017 µg/mL) was taken and adjusted to a neutral pH with 1 M NaOH. The fermentation broth was centrifuged at 4500 rpm and 25° C. for 20 minutes with a high-speed low-temperature centrifuge to obtain a supernatant. The residues were washed with water and then discarded. The supernatant was adjusted to pH 4.0 with 1 M HCl and loaded on an H103 resin column (pre-treated, 2.2 L) for absorption. The H103 pretreatment was performed according to the manual provided by the manufacturer. After absorption, the column was washed with deionized water until the effluent was nearly colorless.

The desorption solution containing pseudomonic acid A was obtained from the resin with 8.3 L of a solvent containing ethanol, salt and water (3320 mL of ethanol, 410 g of ammonium chloride, and the remaining of water), and the ratio of the solvent containing ethanol, salt and water to pseudomonic acid A was 3.0 mL: 22 mg.

After desorption, the content of pseudomonic acid A in the desorption solution was 72%, and the yield of pseudomonic acid A was 52%.

The desorption indexes described in Example 1 of Patent No. CN101591333B are: the content of pseudomonic acid A in the desorption solution collected reaches 70%, and the yield of pseudomonic acid A reaches 90%. The yield reported in the document is significantly different from that in the reproduction experiment.

The invention claimed is:

1. A method for extracting mupirocin comprising:
   a. resin adsorption: adding the resin into a mupirocin fermentation broth and stirring for adsorption, filtering the fermentation broth, rinsing, and collecting the resin, wherein the resin is a nonpolar macroporous adsorption resin, the feeding amount of the resin is 0.02 to 0.05 g mupirocin/g resin, and the pH of the resin adsorption is 5.5 to 6.5;
   b. desorption and concentration: loading the resin collected in step a on a desorption column; soaking the resin with ethyl acetate or acetone, desorbing, and collecting and concentrating the desorption solution; and
   c. extraction: extracting the concentrated desorption solution in step b, and separating a solvent phase; wherein the extraction is a multi-step extraction comprising a first ester solvent extraction, at least one alkaline water extraction, and a second ester solvent extraction in order;
   wherein the first and second ester solvent is ethyl acetate, and the pH of the first and second ester solvent extractions is 3.0 to 5.0;
   the alkaline water is selected from a sodium bicarbonate solution, an ammonium bicarbonate solution or a sodium hydroxide solution, and the pH of the alkaline water is 7.5 to 10.0;
   wherein the alkaline water extraction is repeated once or twice or more times, and the alkaline water phases separated from the extractions are combined for use in the second ester solvent extraction.

2. The method according to claim 1, wherein the solvent phase collected in step c is dehydrated and decolored in sequence.

3. The method according to claim 1, wherein the amount of ethyl acetate or acetone used for the desorption is 2 to 5 times the volume of the resin;

and the flow rate of the desorption is 1/5 to 6/5 times the volume of the resin per hour.

4. The method according to claim 2, wherein the dehydrating agent is selected from anhydrous sodium sulfate, anhydrous magnesium sulfate or anhydrous calcium sulfate;

the amount of the dehydrating agent used is 0.02 to 0.08 kg/L solvent phase;

the decolorant is selected from activated carbon or activated clay;

and the amount of the decolorant used is 1 to 6 g/g dehydrated solvent phase.

5. The method according to claim 1, wherein the first ester solvent extraction is repeated once or twice, and the ester solvent phases separated from the extractions are combined.

6. The method according to claim 5, wherein the second ester solvent extraction is repeated once or twice, and the ester solvent phases separated from the extractions are combined.

\* \* \* \* \*